United States Patent [19]

Merianos et al.

[11] 4,140,798
[45] Feb. 20, 1979

[54] METHOD OF INHIBITING MICROORGANISMS

[75] Inventors: John J. Merianos, Jersey City, N.J.; Harold A. Green, Havertown, Pa.; Alfonso N. Petrocci, Glen Rock, N.J.

[73] Assignee: Kewanee Industries, Inc., Bryn Mawr, Pa.

[21] Appl. No.: 859,945

[22] Filed: Dec. 12, 1977

Related U.S. Application Data

[62] Division of Ser. No. 744,618, Nov. 24, 1976, abandoned.

[51] Int. Cl.$^2$ ............................................. A61K 31/13
[52] U.S. Cl. .................................. 424/325; 260/584 R; 260/584 B; 260/584 C; 424/316
[58] Field of Search ..................... 424/325; 260/584 R, 260/584 C, 584 B

[56] References Cited

U.S. PATENT DOCUMENTS

| | | | |
|---|---|---|---|
| 2,541,678 | 2/1951 | Swaney et al. | 424/325 X |
| 3,067,092 | 12/1962 | Feichtinger et al. | 424/325 X |
| 3,167,475 | 1/1965 | Gottfried et al. | 424/325 X |
| 3,896,171 | 7/1975 | Holtschmidt et al. | 424/325 X |
| 3,905,968 | 9/1975 | Schneider | 260/584 R X |
| 3,965,265 | 6/1976 | Koppensteiner et al. | 424/325 X |

FOREIGN PATENT DOCUMENTS

548484 4/1974 Switzerland .......................... 260/584 B

OTHER PUBLICATIONS

Noren, "J. Polym. Sci., Polym. Chem. Ed.", vol. 13 (3), pp. 693-700, (1975).

*Primary Examiner*—Winston A. Douglas
*Assistant Examiner*—John J. Doll
*Attorney, Agent, or Firm*—Arthur A. Jacobs

[57] ABSTRACT

A method of inhibiting microorganisms by the application of a compound formed by the condensation of dimethylamine and epichlorohydrin in about equimolar proportions.

A high molecular weight condensation product, utilizable as a non-foaming anti-microbial and preservative agent, which is prepared by reacting equimolar proportions of dimethylamine and epichlorohydrin at a relatively low temperature and then maintaining the mixture for a predetermined period of time at a relatively high temperature.

1 Claim, No Drawings

METHOD OF INHIBITING MICROORGANISMS

This application is a division of application Ser. No. 744,618, filed Nov. 24, 1976, now abandoned.

This invention relates to a non-foaming anti-microbial and perservative agent. More specifically, it relates to a high molecular weight anti-microbial and preservative agent made by condensing dimethylamine with epichlorohydrin in approximately a 1:1 molar ratio.

Specifically, it relates to a high molecular weight antimicrobial and preservative product which is made by condensing dimethylamine with one equivalent of epichlorohydrin at low temperature in the neighborhood of 20°–30° C. for about 2 hours, then heating the condensate at a higher temperature at about 40°–90° C. for about 2–12 hours; the higher the temperature, the less the heating time required.

The final product of this process is a very potent anti-microbial. It is, furthermore, a non-foaming anti-microbial which makes it useful in the control of microorganisms in re-circulating water systems such as in paper manufacturing, air conditioners, humidifiers, grinding lubricants, and in those systems where foaming is a burdensome problem, or interferes with normal anti-microbial activity of additives. It is also useful in keeping relatively standing waters, such as swimming pools, free from microbes.

Another feature of the product of the present invention is that it maintains its anti-microbial effectiveness in the presence of non-ionic surfactants or emulsifiers, thereby making it especially useful as a preservative in cosmetic preparations that require or use non-ionic emulsifiers.

The following example illustrates the preparation of a product embodying the present invention:

EXAMPLE 1

110 grams of 22% aqueous solution of dimethylamine ($\frac{1}{2}$ mole) was cooled to about 20°–30° C., and 46.7 grams of epichlorohydrin was added slowly in small portions over a period of about 1 hour, thereby keeping the temperature of the reaction mixture between 20°–30° C. Then, after keeping the reaction mixture at about 20°–30° for an additional 1 hour, it was heated on a steam bath and kept at a temperature of about 40°–90°, under a reflux condenser, for about 2–12 hours, after which it was permitted to cool. The lower the temperature, the longer the heating time required.

Analysis for ionic chloride indicated that about 99% of the halogen from epichlorohydrin had been converted to the product (11.75 found, 11.90 calculated).

Enough water and other volatile material was removed in vacuo to produce a 50% solids solution.

The following examples illustrate the anti-microbial activity of the products of this invention:

EXAMPLE 2

The product made in Example 1 was diluted in distilled water to selected test concentrations, and 50 ml. of these solutions were transferred aseptically to a set of previously sterilized cotton-stoppered 125 ml. Erlenmeyer flasks, wherein each flask had a different concentration of the material to be tested. Each flask was then inoculated with 0.5 ml. of 1/10 nutrient broth dilution of a 24-hour nutrient broth culture of Aereobacter aerogenes.

Another set of flasks containing different concentrations of the product made in Example 1 were similarly prepared and inoculated with 0.5 ml. of a 1/10 nutrient broth dilution of a 24-hour nutrient broth culture of Pseudomonas aeruginosa.

At 30 and 60 minutes following each inoculation, a 1 ml. aliquot was removed from each flask and added to 9 ml. of sterile azolectin/"Tween 80" neutralizer, from which additional 10 fold serial dilutions were prepared in sterile neutralizer solutions.

Agar plates were prepared from $1 \times 10^{-2}$ and $1 \times 10^{-3}$ dilutions.

A control of sterile distilled water was similarly inoculated and aliquots were made at the same intervals and with agar plates at $1 \times 10^{-4}$, $1 \times 10^{-5}$ and $1 \times 10^{-6}$ dilutions.

The number of surviving organisms for various concentrations at different times of exposure was noted, and a comparison was made. In this respect, the same test was run for the same concentrations against the same organisms and the results of the separate tests are listed in separate columns in each table:

Table 1

Product of Example 1 acting for 30 minutes on Aerobacter aerogenes at a concentration of $10.05 \times 10^6$ organisms per ml.:

| Concentration of Product in ppm | Number of Surviving Organisms $\times 10^{-2}$ | | |
|---|---|---|---|
| | Test No. 1 | Test No. 2 | Test No. 3 |
| 10 | 47.5 | 42.5 | — |
| 15 | 36.5 | 30.5 | — |
| 20 | — | 22.5 | — |
| 25 | 8.5 | 8.5 | — |
| 40 | 0 | 0 | 0 |
| 50 | 0 | 0 | 0 |
| 75 | 0 | 0 | 0 |
| 100 | 0 | 0 | 0 |
| 200 | 0 | 0 | 0 |

Table 2

Product of Example 1 acting for 60 minutes on Aerobacter aerogenes at a concentration of $10.05 \times 10^6$ organisms per ml.:

| Concentration of Product in ppm | Number of Surviving Organisms $\times 10^{-2}$ | |
|---|---|---|
| | Test No. 1 | Test No. 2 |
| 10 | 18.5 | 17 |
| 15 | 8.5 | 8 |
| 20 | — | 3 |
| 25 | 0 | 0 |
| 40 | 0 | 0 |
| 50 | 0 | 0 |
| 75 | 0 | 0 |
| 100 | 0 | 0 |
| 200 | 0 | 0 |

Table 3

Product of Example 1 acting for 30 minutes on Pseudomonas aeruginosa at a concentration of $14.05 \times 10^6$ organisms per ml.

| Concentration of Product 1 in ppm | Number of Surviving Organisms $\times 10^{-2}$ | | |
|---|---|---|---|
| | Test No. 1 | Test No. 2 | Test No. 3 |
| 10 | 258.5 | — | — |
| 15 | 195 | — | — |
| 20 | — | 99.5 | — |
| 25 | 48 | 38.5 | — |
| 30 | — | 31.5 | — |
| 40 | 15.5 | 15.5 | — |
| 50 | 5 | 1 | 0 |
| 75 | 0 | 0 | 0 |
| 100 | 0 | 0 | 0 |
| 200 | 0 | 0 | 0 |

Table 4

Product of Example 1 acting for 60 minutes on Pseudomonas aeruginosa at a concentration of $14.05 \times 10^6$ organisms per ml.

| Concentration of Product 1 in ppm | Number of Surviving Organisms $\times 10^{-2}$ | | |
|---|---|---|---|
| | Test No. 1 | Test No. 2 | Test No. 3 |
| 10 | 180 | — | — |
| 15 | 80.5 | — | — |
| 20 | — | 57 | — |
| 25 | 19 | 10.5 | — |
| 30 | — | 5.5 | — |
| 40 | 0 | 0 | 0 |
| 50 | 0 | 0 | 0 |
| 75 | 0 | 0 | 0 |
| 100 | 0 | 0 | 0 |
| 200 | 0 | 0 | 0 |

Tables 1, 2, 3, and 4 show that the product made in Example 1, in testing, caused the complete absence of surviving Aerobacter aerogenes organisms after 30 minutes exposure when applied at a concentration of 40 ppm, and after 60 minutes exposure when applied at a concentration of 25 ppm. Tests against Pseudomonas aeruginosa showed the complete absence of surviving organisms after 30 minutes exposure when applied at a concentration 50–75 ppm, and after 60 minutes exposure when applied at a concentration of 40 ppm.

The following examples show the non-foaming properties:

EXAMPLE 3

A graduated blender cylinder was rinsed with distilled water. 100 ml. of aqueous test solution were added down the walls of the blender so as to cause no foam. The blender was turned to high speed for exactly 5 seconds, and upon turning the blades off, timing was started with a stop watch, and at the same time the foam height was read in mm. from the 100 ml. mark. The foam half-life is defined as the time it takes for liquid to drain out of the foam and reach the 50 ml. mark.

The results were as follows:

Table 5

| Sample | ppm | Foam Height in mm. | Half-Life |
|---|---|---|---|
| Alkyldimethylbenzyl Ammonium Chloride | 50 | 16 | 7.2 Sec. |
| Product of Example 1 | 50 | 0 | 0 |

EXAMPLE 4

A cylinder shake test was used wherein 100 ml. of test solution was gently poured down the walls of a 250 ml. graduated cylinder that has a glass stopper. The cylinder was stoppered and inverted 20 times in 15 seconds, finally resting it in an upright position. The foam height was read in cc. from the base of the foam.

Table 6

| Sample | ppm | Foam Height in cc. | | |
|---|---|---|---|---|
| | | Initial | 1 min. | 5 min. |
| Alkyldimethylbenzyl Ammonium Chloride | 50 | 48 | 35 | 30 |
| Product of Example 1 | 50 | 0 | 0 | 0 |

EXAMPLE 5

Another test used was the standard "Ross-Miles Test" according to the procedure reported in "ASTM standards, Designation 1175-53, Part X, 1958, page 878" which is the ASTM test for foaming properties of surface active materials.

Table 7

| Sample | ppm | Foam Height in cc. | | |
|---|---|---|---|---|
| | | Initial | 1 min. | 5 min. |
| Alkyldimethylbenzyl Ammonium Chloride | 50 | 35 | 30 | 20 |
| Product of Example 1 | 50 | 0 | 0 | 0 |

The results from tables 5, 6, and 7 clearly show that the product made in Example 1 is non-foaming, whereas alkyl dimethyl benzyl quaternary ammonium biocides cause relatively copious foam in aqueous solution.

The invention claimed is:

1. A method of inhibiting microorganisms which comprises applying to said microorganisms an inhibitorily effective amount of a compound formed by the condensation of dimethylamine and epichlorohydrin in about a 1:1 molar ratio at a temperature of about 20° C. to about 30° C. for about 2 hours, and then heating the condensate at a temperature of between about 40° C. to about 90° C. for a period of between about 2 to about 12 hours.

* * * * *